United States Patent

Casci et al.

[11] Patent Number: 6,027,707
[45] Date of Patent: *Feb. 22, 2000

[54] NU-88 ZEOLITE, A PROCESS FOR ITS PREPARATION AND CATALYTIC APPLICATIONS THEREOF

[75] Inventors: John Leonello Casci; Sheena Maberly, both of Cleveland, United Kingdom; Eric Benazzi, Montesson; Loïc Rouleau, Oullins, both of France; Roland Patrick Henney, Northumberland, United Kingdom

[73] Assignee: Institut Francais du Petrole, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/916,363

[22] Filed: Aug. 22, 1997

[30] Foreign Application Priority Data

Aug. 23, 1996 [FR] France ................................ 96 10507

[51] Int. Cl.⁷ .................... C01B 39/48; B01J 29/068; B01J 29/072; B01J 29/076
[52] U.S. Cl. .................... 423/705; 423/706; 423/718; 585/273; 585/467; 585/419; 585/481; 585/482; 585/475; 585/520; 585/531; 585/653; 585/660; 585/666; 585/721; 585/739; 208/122; 208/124; 502/64; 502/65; 502/66; 502/67
[58] Field of Search ................... 423/702, 706, 423/705, 718; 585/419, 273, 481, 482, 475, 467, 721, 520, 531, 653, 660, 739, 666; 208/122, 124; 502/64, 65, 66, 67

[56] References Cited

U.S. PATENT DOCUMENTS

| | | | |
|---|---|---|---|
| 4,508,837 | 4/1985 | Zones ........................................ | 502/62 |
| 4,539,193 | 9/1985 | Valyocsik .................................. | 423/718 |
| 4,676,958 | 6/1987 | Zones . | |
| 4,826,667 | 5/1989 | Zones et al. ............................. | 423/718 |
| 4,941,963 | 7/1990 | Valyocsik . | |
| 5,068,096 | 11/1991 | Valyocsik . | |
| 5,108,579 | 4/1992 | Casci ........................................ | 423/718 |
| 5,173,281 | 12/1992 | Chang et al. ............................ | 423/718 |
| 5,190,736 | 3/1993 | Hellrig et al. ........................... | 423/718 |

FOREIGN PATENT DOCUMENTS

| | | |
|---|---|---|
| 0 135 658 | 4/1985 | European Pat. Off. . |
| 94/00384 | 1/1994 | WIPO . |

Primary Examiner—Mark L. Bell
Assistant Examiner—David Sample
Attorney, Agent, or Firm—Millen, White, Zelano & Branigan, P.C.

[57] ABSTRACT

The invention concerns NU-88 zeolite, characterized by:
i) a chemical composition with the following formula, expressed in terms of the mole ratios of the oxides for the anhydrous state:

$$100\, XO_2, mY_2O_3, pR_{2/n}O$$

where m is 10 or less;

p is 20 or less;

R represents one or more cations with valency n;

X represents silicon and/or germanium;

Y represents one or more of the following elements: aluminium, iron, gallium, boron, titanium, vanadium, zirconium, molybdenum, arsenic, antimony, chromium and manganese; and ii) an X ray diffraction diagram, in its as synthesized state, which comprises the results shown in Table 1 of the description.

The invention also concerns the preparation of the zeolite, any catalyst containing the zeolite and any catalytic process using such a catalyst.

35 Claims, 2 Drawing Sheets

FIG.1

NU-88 ZEOLITE, A PROCESS FOR ITS PREPARATION AND CATALYTIC APPLICATIONS THEREOF

SUMMARY OF THE INVENTION

The present invention concerns a novel zeolite, hereinafter termed zeolite NU-88, a process for its preparation, any catalyst containing the zeolite and any catalytic process using the catalyst.

In accordance with the present invention, the NU-88 zeolite is characterized by:

i) a chemical composition with the following formula, expressed in terms of the mole ratios of the oxides for the anhydrous state:

$$100\ XO_2,\ mY_2O_3,\ pR_{2/n}O$$

where m is 10 or less;

p is 20 or less;

R represents one or more cations with valency n;

X represents silicon and/or germanium, preferably silicon;

Y is selected from the group formed by the following elements: aluminium, iron, gallium, boron, titanium, vanadium, zirconium, molybdenum, arsenic, antimony, chromium and manganese, Y preferably being aluminium; and ii) an X ray diffraction diagram, in its as synthesized state, which comprises the results shown in Table 1.

TABLE 1

X ray diffraction diagram for NU-88 zeolite (as synthesized state)

| $d_{hkl}$ ($10^{-10}$ m) | $I/I_{max}$ |
|---|---|
| 12.1 ± 0.35 | s or vs (1) |
| 11.0 ± 0.30 | s (1) |
| 9.88 ± 0.25 | m (1) |
| 6.17 ± 0.15 | w |
| 3.97 ± 0.09 | vs (2) |
| 3.90 ± 0.08 | vs (2) |
| 3.80 ± 0.08 | w (2) |
| 3.66 ± 0.07 | vw |
| 3.52 ± 0.07 | vw |
| 3.27 ± 0.07 | vw |
| 3.09 ± 0.06 | w |
| 2.91 ± 0.06 | w |
| 2.68 ± 0.06 | vw |
| 2.49 ± 0.05 | vw |
| 2.20 ± 0.05 | vw |
| 2.059 ± 0.05 | w |
| 1.729 ± 0.04 | vw |

(1) These peaks were not resolved and formed part of a feature.
(2) these peaks were not resolved and formed part of the same feature.

The invention also concerns NU-88 in its hydrogen form, termed H-NU-88, produced by calcining and/or ion exchange as will be described below. H-NU-88 zeolite has an X ray diffraction diagram which comprises the results shown in Table 2.

TABLE 2

X ray diffraction diagram for NU-88 zeolite (hydrogen form)

| $d_{hkl}$ ($10^{-10}$ m) | $I/I_{max}$ |
|---|---|
| 12.1 ± 0.35 | vs (1) |
| 11.0 ± 0.30 | s or vs (1) |
| 9.92 ± 0.25 | w or m (1) |
| 8.83 ± 0.20 | vw |
| 6.17 ± 0.15 | w |
| 3.99 ± 0.10 | s or vs (2) |
| 3.91 ± 0.08 | vs (2) |
| 3.79 ± 0.08 | w or m (2) |
| 3.67 ± 0.07 | vw |
| 3.52 ± 0.07 | vw |
| 3.09 ± 0.06 | w |
| 2.90 ± 0.06 | w |
| 2.48 ± 0.05 | w |
| 2.065 ± 0.05 | w |
| 1.885 ± 0.04 | vw |
| 1.733 ± 0.04 | vw |

(1) These peaks were not resolved and formed part of a feature.
(2) these peaks were not resolved and formed part of the same feature.

These diagrams were obtained using a diffractometer and a conventional powder method utilising the $K_\alpha$ line of copper, Cu K alpha. From the position of the diffraction peaks represented by the angle 2θ, the characteristic interplanar distances $d_{hkl}$ of the sample can be calculated using the Bragg equation. The intensity is calculated on the basis of a relative intensity scale attributing a value of 100 to the line representing the strongest peak on the X ray diffraction diagram, and then:

very weak (vw) means less than 10;
weak (w) means less than 20;
medium (m) means in the range 20 to 40;
strong (s) means in the range 40 to 60;
very strong (vs) means more than 60.

The X ray diffractograms from which the data are obtained (spacing d and relative intensities) are characterized by large reflections with a large number of peaks forming shoulders on other peaks of higher intensity. Some or all of the shoulders may not be resolved. This may be the case for samples with poor crystallinity or for samples with crystals which are small enough to produce significant broadening of the X rays. This can also be the case when the equipment or operating conditions used to produce the diagram differ from those used in the present case.

NU-88 zeolite is considered to have a novel basic structure or topology which is characterized by its X ray diffraction diagram. NU-88 zeolite in its "as synthesized state" has substantially the X ray diffraction characteristics shown in Table 1, and is thus distinguished from prior art zeolites. The invention also concerns any zeolite with the same structural type as that of NU-88 zeolite.

Figure 1:
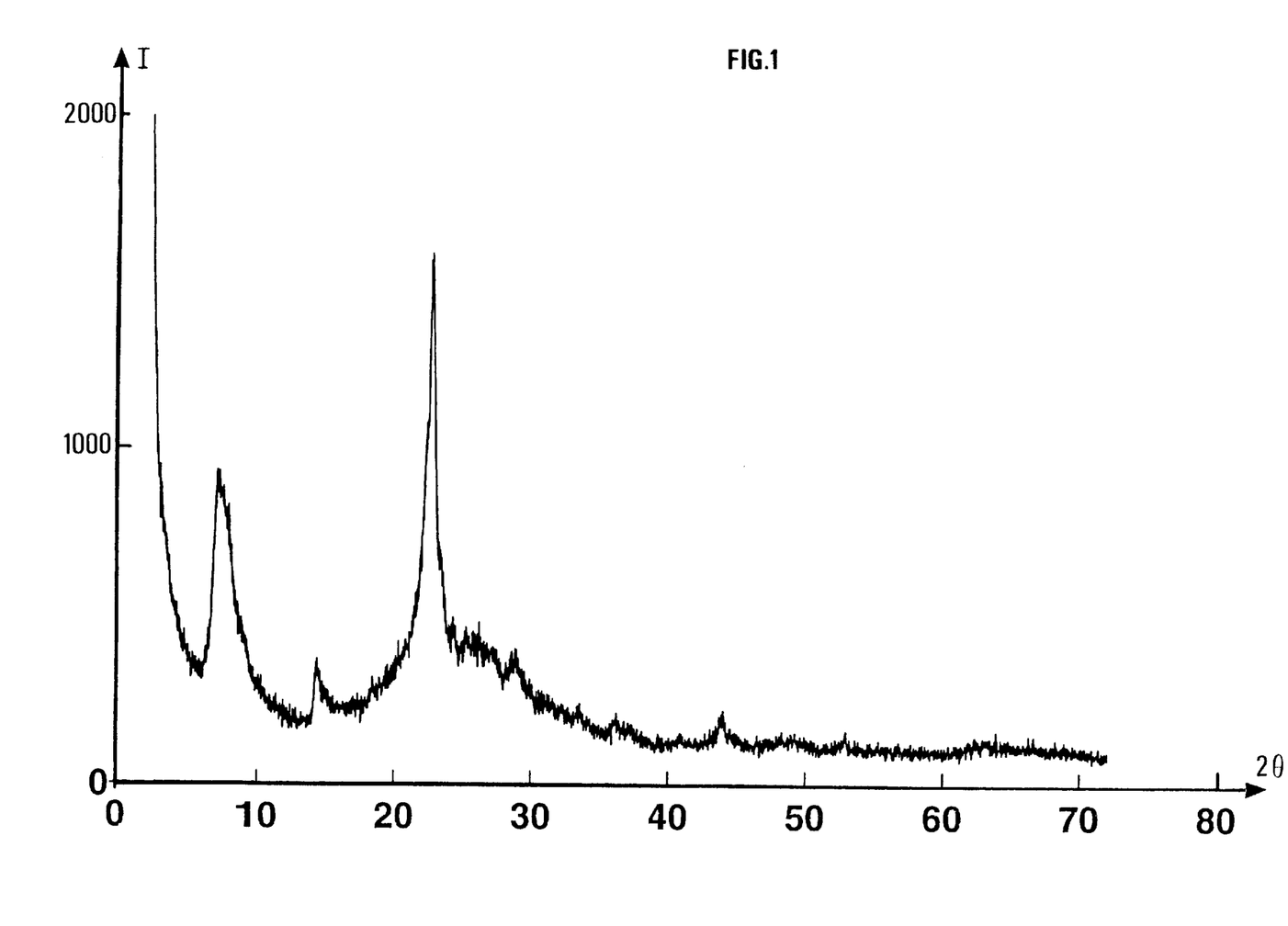
FIG. 1 is an X-ray diffraction pattern of as-synthesized NU-88.
Figure 2:
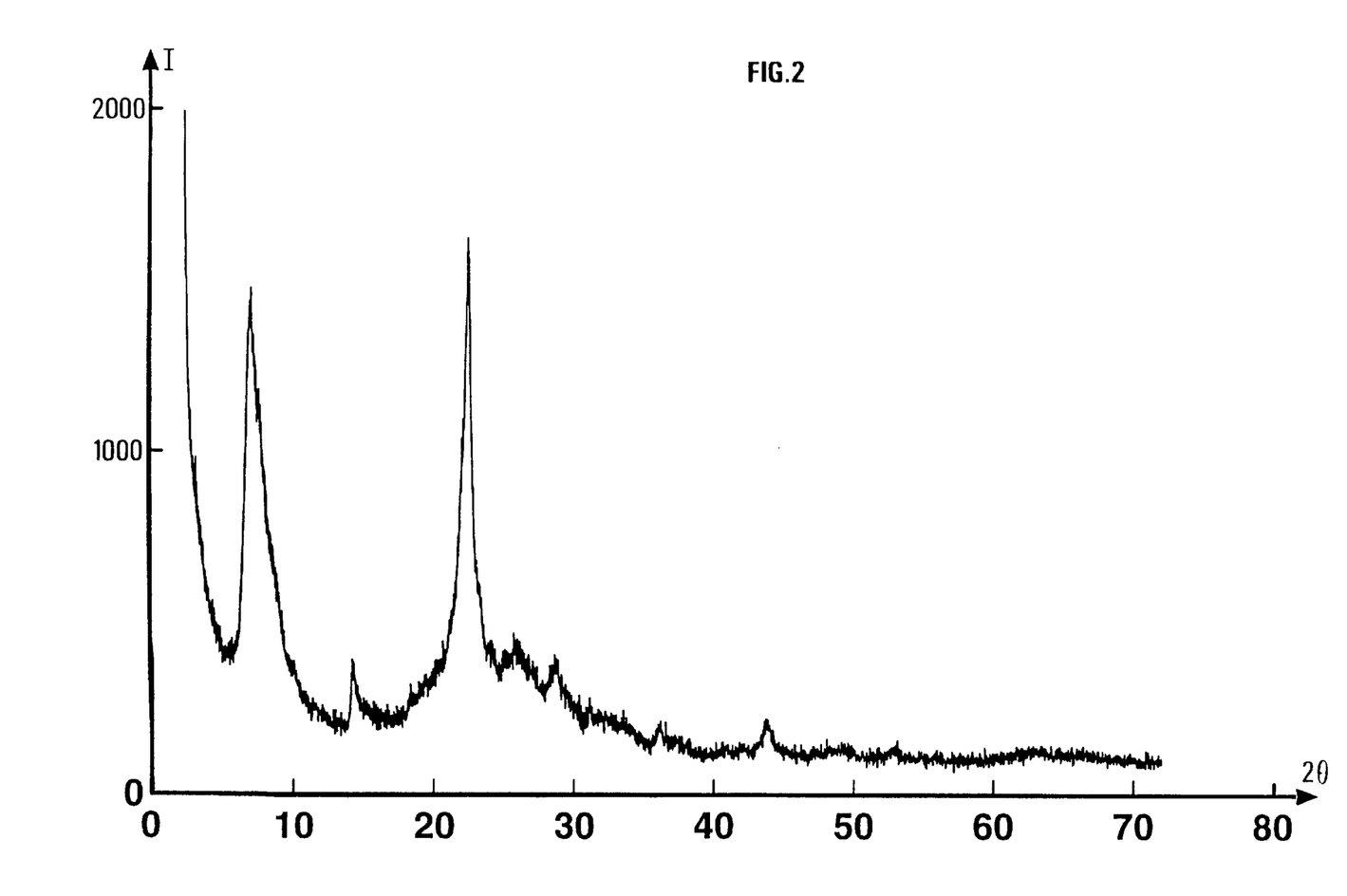
FIG. 2 is an X-ray diffraction pattern of calcined NU-88.

Tables 1 and 2 and the diffractograms of FIGS. 1 and 2 are relatively unusual for zeolitic structures. Thus these data appear to indicate that NU-88 zeolite has a defective structure.

In the chemical composition defined above, m is generally in the range 0.1 to 10, preferably 0.2 to 9, and more preferably 0.6 to 8; it appears that NU-88 zeolite is generally obtained in a very pure form when m is in the range 0.6 to 8.

This definition also includes NU-88 zeolite in its "as synthesized state", as well as the forms obtained on dehydration and/or calcining and/or ion exchange. The term "in its as synthesized state" designates the product obtained by synthesis and washing, with or without drying or dehydration. In its "as synthesized state", NU-88 zeolite may contain a cation of metal M, which is an alkali, in particular sodium, and/or ammonium, and it may contain organic nitrogen-containing cations such as those described below or their decomposition products, or precursors thereof. These organic nitrogen-containing cations are designated here by the letter Q, which also includes the decomposition products and precursors of the organic nitrogen-containing cations.

Thus NU-88 zeolite in its "as synthesized state" (not calcined) is characterized by:

i) a chemical composition with the following formula, expressed in terms of the mole ratios of the oxides for the anhydrous state:

100 $XO_2$: 10 or less $Y_2O_3$: 10 or less Q: 10 or less $M_2O$, where

X represents silicon and/or germanium;

Y is selected from the group formed by the following elements: aluminium, iron, gallium, boron, titanium, vanadium, zirconium, molybdenum, arsenic, antimony, chromium and manganese;

M is at least one alkali metal cation (group IA of the periodic table) and/or ammonium; and Q is at least one organic nitrogen-containing cation or a precursor of an organic nitrogen-containing cation or a decomposition product of an organic nitrogen-containing cation;

ii) an X ray diffraction diagram, in its as synthesized state, which comprises the results shown in Table 1.

The compositions indicated above for NU-88 zeolite are given for the anhydrous state, since the NU-88 zeolite in its "as synthesized state" and activated forms of the NU-88 zeolite, i.e., resulting from calcining and/or ion exchange, may contain water. The mole ratio of $H_2O$ of such forms, including NU-88 zeolite in its "as synthesized state", depends on the conditions under which it is prepared and stored after synthesis or activation. The mole quantities of water contained in these forms are typically in the range 0 to 100% $XO_2$.

The calcined forms of NU-88 zeolite do not contain any organic nitrogen-containing compound, or contain a lesser quantity than the "as synthesized state", since the major portion of the organic substance has been eliminated, generally by heat treatment consisting of burning off the organic substance in the presence of air, the hydrogen ion ($H^+$) thus forming the other cation.

Thus the NU-88 zeolite in its hydrogen form is characterized by:

i) a chemical composition with the following formula, expressed in terms of the mole ratios of the oxides for the anhydrous state:

100 $XO_2$: 10 or less $Y_2O_3$: 10 or less $M_2O$, where

X represents silicon and/or germanium;

Y is selected from the group formed by the following elements: aluminium, iron, gallium, boron, titanium, vanadium, zirconium, molybdenum, arsenic, antimony, chromium and manganese; and M is at least one alkali metal cation (group IA of the periodic table) and/or ammonium; and/or hydrogen;

ii) an X ray diffraction diagram, in its as synthesized state, which comprises the results shown in Table 2.

Of the NU-88 zeolite forms which can be obtained by ion exchange, the ammonium form ($NH_4^+$) is important as it can readily be converted into the hydrogen form by calcining. The hydrogen form and forms containing metals introduced by ion exchange will be described below. In some cases, the fact that the zeolite of the invention is subjected to the action of an acid can give rise to partial or complete elimination of a base element such as aluminium, as well as generation of the hydrogen form. This may constitute a means of modifying the composition of the substance after it has been synthesized.

The invention also includes NU-88 zeolite in its hydrogen form, termed H-NU-88, produced by calcining and ion exchange as will be described below.

In one aspect, the invention concerns NU-88 zeolite at least partially in its $H^+$ form (as defined above) or in its $NH_4^+$ form or in its metal form, said metal being selected from the group formed by groups IA, IB, IIA, IIB, IIIA, IIIB (including the rare earths), VIII, Sn, Pb and Si, preferably at least partially in its $H^+$ form or at least partially in its metal form. This type of zeolite generally has an X ray diffraction diagram which includes the results shown in Table 1.

The invention also concerns a process for the preparation of NU-88 zeolite in which an aqueous mixture is reacted which comprises at least one source of at least one oxide $XO_2$, at least one source of at least one oxide $Y_2O_3$, optionally at least one source of at least one oxide $M_2O$, and at least one organic nitrogen-containing cation Q, or a precursor of an organic nitrogen-containing cation or a decomposition product of an organic nitrogen-containing cation, the mixture generally having the following molar composition:

$XO_2/Y_2O_3$ at least 10, preferably 10 to 60, more preferably 15 to 50;

$(R_{1/n})OH/XO_2$ of 0.01 to 2, preferably 0.05 to 1, more preferably 0.10 to 0.75;

$H_2O/XO_2$ of 1 to 500, preferably 5 to 250, more preferably 25 to 75;

$Q/XO_2$ of 0.005 to 1, preferably 0.02 to 1, more preferably 0.05 to 0.5;

$L_pZ/XO_2$ of 0 to 5, preferably 0 to 1, more preferably 0 to 0.25;

where

X is silicon and/or germanium, preferably silicon;

Y is selected from the group formed by the following elements: aluminium, iron, boron, titanium, vanadium, zirconium, molybdenum, arsenic, antimony, gallium, chromium, manganese, Y preferably being aluminium;

R is a cation with valency n which comprises M (an alkali metal and/or ammonium cation) and/or Q (an organic nitrogen-containing cation or a precursor thereof or a decomposition product thereof);

$L_pZ$ is a salt, Z being an anion with valency p and L an alkali metal ion or ammonium ion which may be similar to M or a mixture of M and a further alkali metal or ammonium ion required to balance anion Z, and Z may comprise an acid radical which is added, for example, in the form of a salt of L or an aluminium salt.

In some cases, it may be of advantage to add a salt $L_pZ$. Thus in a preferred preparation process, the aqueous medium comprises said salt. Examples of Z are the radicals of strong acids such as bromide, chloride, iodide, sulphate, phosphate or nitrate, or the radicals of weak acids such as organic acid radicals, for example citrate or acetate. While $L_pZ$ is not essential, it may accelerate crystallisation of the NU-88 zeolite from a reaction medium and it may also affect the size and shape of crystals containing the NU-88 zeolite. In all cases, the reaction is carried out until crystallisation occurs.

A large number of zeolites have been prepared with organic nitrogen-containing cations, and heterocyclic nuclei in particular have been widely used for zeolite synthesis. ZSM-12 zeolite has been synthesized using different types of heterocycles, for example the pyrrolidinium based structure:

and the piperidinium based structure:

has been described by Rosinski et al. in U.S. Pat. No. 4,391,785 (Mobil).

The synthesis of TPZ-12 zeolite, which is a structural isomer of ZSM-12 zeolite, has been described by Teijin in European patent application EP-A-0 135 658. Structures considered to be suitable for the synthesis of pure TPZ-12 are based on bis-pyrrolidinium:

and on bis-piperidinium:

where n is varied from 4 to 6, and $R_1$ and $R_2$ are H, methyl, ethyl, propyl or butyl.

ZSM-12 has also been synthesized with structures comprising more than one heterocyclic nucleus. The use of a polymethonium type compound:

has been described by Valyocsik in U.S. Pat. No. 4,539,193 (Mobil).

The use of structures based on bis(butylpyrrolidinium) with general formula:

has been described by Valyocsik in U.S. Pat. No. 4,941,963 (Mobil). Four structures were tested by varying n from 4 to 7. Pure ZSM-11 zeolite could only be synthesized when n was 6 or 7.

In accordance with the invention, Q is preferably a bis (methyl-pyrrolidinium) cation or a decomposition product thereof or a precursor thereof, with general formula:

where n=4, 5 or 6, or Q is butane-1,4-bis(bisquinuclidinium) bromide, or a decomposition product thereof or a precursor thereof, with the following chemical formula:

As an example, Q is hexane-1,6-bis(methylpyrrolidinium) bromide, pentane-1,5-bis(methylpyrrolidinium) bromide, butane-1,4-bis(methylpyrrolidinium) bromide, or Q is butane-1,4-bis(quinuclidinium) bromide.

M and/or Q can be added in the form of hydroxides or the salts of mineral acids provided that the $(R_{1/n})OH/XO_2$ ratio is satisfied.

Such substances can be used in the form of simple mixtures or they can be pre-heated together in the reactor, preferably in solution, before adding the other reactants required for the synthesis of the NU-88 zeolite.

Cation M is preferably an alkali metal, in particular sodium; $XO_2$ is preferably silica ($SiO_2$) and the oxide $Y_2O_3$ is preferably alumina ($Al_2O_3$).

In the preferred case when X is silicon, the source of the silicon can be any one of those which are currently used in the zeolite synthesis, for example solid or powdered silica, silicic acid, colloidal silica or dissolved silica. Examples of powdered silica are precipitated silicas, in particular those obtained by precipitation from a solution of an alkali metal silicate such as that known as "KS 300" manufactured by AKZO, and similar products, aerosil silicas, fumed silicas, for example "CAB-O-SIL" and silica gels in suitable concentrations for use in reinforcing pigments for rubber and silcone rubber. Colloidal silicas with different particle sizes can be used, for example those with an average equivalent diameter in the range 10 to 15 μm or in the range 40 to 50 μm such as those sold under the trade names "LUDOX", "NALCOAG" and "SYTON". Dissolved silicas which can be used also include commercially available soluble glass silicates containing 0.5 to 6.0, in particular 2.0 to 4.0, moles of $SiO_2$ per mole of alkali metal oxide, "active" alkali metal silicates as defined in United Kingdom patent GB-A-1 193 254, and silicates obtained by dissolving silica in an alkali metal hydroxide or a quaternary ammonium hydroxide or a mixture thereof.

In the preferred case where Y is aluminium, the alumina source is preferably sodium aluminate or an aluminium salt, for example aluminium chloride, nitrate or sulphate, an aluminium alkoxide or alumina itself, preferably in its hydrated or hydratable form, such as colloidal alumina, pseudoboehmite, gamma alumina or alpha or beta trihydrate. Mixtures of the sources cited above can also be used.

Some or all of the alumina and silica sources can optionally be added in the form of an aluminosilicate.

The reaction mixture is generally reacted at an autogenous pressure, optionally by adding gas, for example nitrogen, at a temperature which is in the range 85° C. to 200° C., preferably in the range 120° C. to 180° C., and more preferably at a temperature which does not exceed 165° C., until NU-88 zeolite crystals are formed, the time period generally being between 1 hour and several months depending on the composition of the reaction mixture and the temperature used. The reaction can be carried out by stirring, which is preferable as it reduces the reaction time and increases the purity of the product.

It may be of advantage to use seeds to reduce the time required for crystal formation and/or the total time required for crystallisation. It may also be of advantage to encourage formation of NU-88 zeolite. Such seeds comprise zeolites, in particular crystals of NU-88 zeolite. The crystalline seeds are generally added in a proportion which is in the range 0.01% to 10% by weight of the silica used in the reaction mixture.

At the end of the reaction, the solid phase is recovered by filtering then washing; it is then ready for subsequent steps such as drying, dehydration and calcining and/or ion exchange.

If the reaction product contains alkali metal ions, these must be at least partially eliminated to prepare the hydrogen form of NU-88 zeolite, by ion exchange with an acid, in particular a mineral acid such as hydrochloric acid and/or using an ammonium compound obtained by ion exchange with a solution of an ammonium salt such as ammonium chloride. Ion exchange can be effected by forming a thick suspension, repeating once or more, in an ion exchange solution. The zeolite is generally calcined before carrying out ion exchange to eliminate all absorbed organic substances in order to facilitate ion exchange. All of the operating conditions of such an ion exchange step are known to the skilled person.

In general, the cation(s) of the NU-88 zeolite can be replaced by any metal cation or cations, in particular those from groups IA, IB, IIA, IIB, IIIA, IIIB (including the rare earths), and VIII (including the noble metals) of the periodic table, and by tin, lead and bismuth. Exchange is normally carried out using a solution containing a suitable cation salt, in a manner which is known to the skilled person.

The invention also concerns the composition of a catalyst containing NU-88 zeolite. Thus in one aspect, the invention provides a catalyst comprising an NU-88 zeolite as described above or prepared using the preparation process described above. The invention also concerns a catalyst comprising such an NU-88 zeolite, and which further comprises a binder or at least one support or at least one other zeolite of at least one metal selected from the group formed by the elements Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Re and Rh.

In the catalysts of the invention, $XO_2$ is preferably silica and $Y_2O_3$ is preferably alumina. Such catalysts can be used in a large number of catalytic processes and with a wide range of supply feeds.

Forms of NU-88 zeolite which can be used for catalysis generally include the hydrogen and ammonium forms prepared using the methods described above. However, the catalysts of the invention comprising NU-88 zeolite can also contain one or more elements, in particular metals or their cations, or compounds of these elements, in particular metal oxides. These catalysts can be prepared by ion exchange or by impregnating the NU-88 zeolite with said element, cation or compound, or with a suitable precursor of said cation or compound. Such an ion exchange or impregnation step can be carried out on the NU-88 zeolite which is at least partially, preferably almost completely, in its "as synthesized state", which may or may not be calcined, in its hydrogen form and/or in its ammonium form and/or in any other exchanged form (metallic or non metallic).

When a form of NU-88 zeolite containing a metal is prepared by ion exchange, it may be desirable to exchange the metal completely, meaning that substantially all of the exchangeable sites are occupied by that metal. Such forms may be of particular application to separation processes. In the majority of cases, however, it is preferable to carry out only partial exchange of the metal, the remaining sites being occupied by another cation, in particular hydrogen or ammonium cations. In some cases, it may be desirable to introduce two or more metal cations by ion exchange.

When the NU-88 zeolite is impregnated with a metallic compound to form a catalyst, the metallic compound can be added in a suitable proportion, but a maximum proportion of 20% by weight is generally sufficient for the majority of applications; for some applications, 10% by weight is not generally exceeded, and quantities of up to 5% are often appropriate. Impregnation can be carried out using any suitable known method for catalyst preparation.

The metal-exchanged forms or the metallic compound-impregnated forms can be used as they are or they can be treated to produce an active derivative. These treatments include reduction, for example in an atmosphere containing hydrogen, to produce a metal or other reduced forms. These treatments can be carried out at an appropriate stage in the preparation of the catalyst or they can readily be carried out in the catalytic reactor.

Catalytic compositions comprising NU-88 zeolite can, if desired, be combined with a mineral matrix which is either catalytically inert or catalytically inactive. The matrix can be used solely as a binder to keep the zeolite particles together, or it can be in a particular shape, for example a pellet or extrusion product, or it can act as an inert diluting agent, for example to control the activity per unit weight of the catalyst. When the mineral matrix or diluent themselves have catalytic activity, they can form an effective part of the zeolite-matrix catalytic composition. Suitable mineral matrices and diluents include substances which are conventionally used as catalyst supports such as silica, the different forms of alumina, clays such as bentonites, montmorillonites, sepiolite, attapulgite, fuller's earth and porous synthetic materials such as silica-alumina, silica-zirconia, silica-thoria, silica-glucina or silica-titanium dioxide. Combinations of matrices can be used within the context of the present invention, in particular combinations of inert matrices and matrices with catalytic activity.

When the NU-88 zeolite is associated with a mineral matrix substance or with a plurality of such substances, the proportion of matrix substance(s) in the total composition can generally be up to 90% by weight, preferably up to 50% by weight, and more preferably up to 30% by weight.

For certain applications, a further zeolite or molecular sieve can be used conjointly with the NU-88 zeolite to form a catalyst. Such a combination can be used as it is or combined with one or more of the matrix substances described above. A particular example of the use of such a composition is its use as an additive for a fluid catalytic cracking catalyst, when the NU-88 zeolite is preferably used in a proportion of 0.5% to 5% by weight of the total catalyst.

For other applications, the NU-88 zeolite can be combined with another catalyst such as platinum on alumina.

Any method which is suitable for mixing the NU-88 zeolite with an organic matrix and/or another zeolite can be used, in particular that adapted to the final form in which the catalyst is used, for example an extruded, pelletized or granulated product.

If NU-88 zeolites are used to form a catalyst conjointly with a metallic component (for example a hydrogenation/dehydrogenation component or another metal with catalytic activity) in addition to the mineral matrix, the metallic component can be exchanged or impregnated into the NU-88 zeolite itself before adding the matrix substance, or it can be added to the zeolite-matrix composition. For certain applications, it may be of advantage to add the metallic component to all or part of the matrix substance before mixing the latter with the NU-88 zeolite.

A wide range of hydrocarbon conversion catalysts comprising NU-88 zeolite can be prepared by ion exchange or by impregnating the zeolite with one or more cations or oxides derived from elements such as: Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Re and Rh.

When catalysts comprising NU-88 zeolite contain one or more hydrogenation/dehydrogenation components such as the metals Ni, Co, Pt, Pd, Re or Rh, these components can be introduced by ion exchange or by impregnating with a suitable compound of this metal.

Catalytic compositions comprising NU-88 zeolite can be used in reactions involving saturated and unsaturated aliphatic hydrocarbons, aromatic hydrocarbons, organic oxygen-containing compounds and organic compounds containing nitrogen and/or sulphur, also organic compounds containing other functional groups.

Thus in another aspect, the invention concerns any catalytic process in which NU-88 zeolite is comprised in the catalyst. In general, catalyst compositions containing NU-88 zeolite can be effectively used to carry out reactions of isomerisation, transalkylation and dismutation, alkylation and dealkylation, dehydration and hydration, oligomerisation and polymerisation, cyclisation, aromatization, cracking, hydrogenation and dehydrogenation, oxidation, halogenation, amine synthesis, hydrodesulpurization, hydrodenitration, catalytic elimination of oxides of nitrogen (either, as is preferable, by reduction, generally using nitrogen-containing compounds or using hydrocarbons, or by decomposition), ether formation and hydrocarbon conversion and the synthesis of organic compounds in general.

The processes mentioned above can be carried out either in the liquid phase, or in the vapour phase, under conditions selected so as to be the most suitable for each individual reaction. As an example, reactions carried out in the vapour phase can comprise the use of fluid bed, fixed bed or moving bed operations. Diluents can be used if necessary. Depending on the process used, suitable diluents may be inert gases (such as nitrogen or helium), hydrocarbons, carbon dioxide, water or hydrogen. The diluent can be inert or it can have a chemical action. It may be of advantage, in particular if hydrogen is used, to include a metallic component such as a hydrogenation/dehydrogenation component, for example one or more of the metals Ni, Co, Pt, Pd, Re or Rh in the catalyst composition.

The present invention also concerns any hydrocarbon conversion process during which an alkylbenzene or a mixture of alkylbenzenes is brought into contact with a catalyst containing NU-88 zeolite in the liquid or vapour phase, under isomerisation conditions.

Isomerisation reactions for which catalysts containing NU-88 zeolite are particularly useful are those comprising alkanes and substituted aromatic molecules, in particular xylenes. These reactions can include those which can be carried out in the presence of hydrogen. Catalyst compositions containing NU-88 zeolite which are of particular application in isomerisation reactions include those in which the NU-88 zeolites is present in the acid form ($H^+$), in the form obtained after ion exchange, in the form containing metals or in combinations of these forms. Forms in which the metal is a hydrogenation/dehydrogenation component such as Ni, Co, Pt, Pd, Re or Rh are of particular application.

Particular isomerisation reactions for which a catalyst containing NU-88 zeolite are of use include isomerisation and hydro-isomerisation of xylenes, or of paraffins, in particular normal $C_4$ to $C_{10}$ hydrocarbons, or the isomerisation of olefins, and catalytic dewaxing.

Isomerisation and hydro-isomerisation of xylene can be carried out in the liquid or vapour phase. In the liquid phase, suitable isomerisation conditions include a temperature which is in the range 0° C. to 350° C., a pressure which is in the range 0.1 to 20 MPa (absolute), preferably in the range 0.5 to 7 MPa (absolute), and when using a flow system, a weight hourly space velocity (WHSV) which is preferably in the range 1 to 30 $h^{-1}$ based on the total catalyst composition. A diluent can optionally be present, preferably one or more thereof having a high critical temperature under the isomerisation conditions. The diluent, if used, can comprise 1% to 90% by weight of the feed. The isomerisation and hydro-isomerisation reactions for xylene in the vapour phase are carried out at a temperature which is in the range 100° C. and 600° C., preferably in the range 200° C. to 500° C., at a pressure which is in the range 0.05 to 10 MPa (absolute), preferably between 0.1 and 5 MPa (absolute), and at a weight hourly space velocity (WHSV) of up to 80 based on the total catalyst composition.

When xylene is isomerised in the presence of hydrogen (in the vapour phase), the hydrogen/dehydrogenation component which is preferably used is Pt or Ni. The hydrogenation/dehydrogenation component is generally added in a proportion which is in the range 0.5% to 2% of the total catalyst weight. Supplemental metals or metal oxides can be present in the catalyst composition.

When xylene is isomerised, ethylbenzene can be present in the xylene feed in a proportion which can reach 40% by weight. With catalyst compositions which include NU-88 zeolite, ethylbenzene generally transalkylates with itself and with xylenes to form heavier and lighter aromatic compounds. Ethylbenzene generally also reacts to form benzene and light gas, in particular at temperatures of more than 400° C. With such xylene feeds containing ethylbenzene, when the reaction is carried out in the presence of hydrogen with a catalytic composition comprising NU-88 zeolite and a hydrogenation/dehydrogenation component, a certain portion of the ethylbenzene is transformed to xylenes by isomerisation. It may also be of advantage to carry out the xylene isomerisation reactions in the presence of a hydrocarbon compounds, in particular a paraffin or a naphthene, with or without the complementary presence of hydrogen. The hydrocarbon appears to improve catalyst performance in that reactions which cause a loss of xylenes are suppressed and, in particular when the reactions are carried out in the absence of hydrogen, the lifetime of the catalyst is increased.

The present invention also concerns a process for converting hydrocarbons in which one or more alkylated aromatic compounds are brought into contact with a catalyst containing NU-88 zeolite under transalkylation conditions, in the vapour or liquid phase.

Catalysts containing NU-88 zeolite are particularly useful in transalkylation and/or dismutation reactions, in particular in reactions involving aromatic molecules which are mono-, di-, tri- or tetrasubstituted with alkyl groups, in particular toluene and xylenes.

Catalyst compositions containing NU-88 zeolite which have been found to be of particular application for transalkylation and/or dismutation reactions include compositions in which the NU-88 component is present in its acid form (H+), the form obtained by cation exchange, or other forms containing metals or combinations of these different forms. The acid form and the form in which the metal is a hydrogenation/dehydrogenation component such as Ni, Co, Pt, Pd, Re or Rh are particularly effective.

Particular examples of important processes are the dismutation of toluene and the reaction of toluene with aromatic compounds containing at least 9 carbon atoms per molecule, for example trimethylbenzenes.

Toluene dismutation can be carried out in the vapour phase, and in the presence or absence of hydrogen, although it is preferable to operate in the presence of hydrogen since this helps to suppress catalyst deactivation. The most favourable reaction conditions are: temperature in the range 250° C. to 650° C., preferably in the range 300° C. to 550° C.; pressure in the range 0.03 to 10 MPa (absolute), preferably in the range 0.1 to 5 MPa (absolute); weight hourly space velocity (WHSV) up to 50 (based on the total catalyst composition).

When toluene dismutation is carried out in the presence of hydrogen, the catalyst can optionally contain a hydrogenation/dehydrogenation component. Preferably, a hydrogenation/dehydrogenation component such as Pt, Pd or Ni is used. The hydrogenation/dehydrogenation component is normally added in a concentration which can reach 5% by weight of the total catalyst composition. Complementary metals and/or metal oxides can be present in the catalyst composition, for example up to 5% by weight of the total catalyst composition.

The present invention also concerns a process for the conversion of hydrocarbons in which an olefinic or aromatic compound is brought into contact with a suitable alkylating compound under alkylation conditions, in the vapour phase or in the liquid phase, and with a catalyst containing NU-88 zeolite.

Examples of alkylation reactions for which catalysts containing NU-88 zeolite are of particular use are the alkylation of benzene or aromatic molecules substituted with methanol or an olefin or an ether. Specific examples of such processes are the methylation of toluene, the synthesis of ethylbenzene and the formation of ethyltoluene and cumene. The alkylation catalysts used in processes in accordance with this implementation of the invention can comprise other substances, in particular metal oxides, which can improve catalytic performance.

Because a catalyst containing NU-88 zeolite is used, hydrocarbons can be produced by oligomerisation, cyclisation and/or aromatization reactions of unsaturated compounds such as ethene, propene or butene, or of saturated compounds such as propane or butane or of mixtures of hydrocarbons such as light naphthas. For some reactions, in particular aromatization reactions, the catalyst may usefully contain a metal or metal oxide, in particular platinum, gallium, zinc or oxides thereof.

Catalysts containing NU-88 zeolite are used for a wide range of cracking reactions, among them cracking of olefins, paraffins or aromatic compounds, or mixtures thereof. Using NU-88 zeolite as a fluid catalytic cracking additive is particularly useful in improving the cracking reaction product. NU-88 zeolite can also be used as a component of a catalyst for catalytic dewaxing in hydrocracking processes.

Hydrogenation and/or dehydrogenation processes, for example the dehydrogenation of alkanes to the corresponding olefins, are effectively carried out by bringing the appropriate feed into contact, under suitable conditions, with a catalyst containing NU-88 zeolite, in particular when the latter also comprises a hydrogenation/dehydrogenation component such as Ni, Co, Pt, Pd, Re or Ru.

A catalyst containing NU-88 zeolite is also useful for ether formation, in particular when reacting two alcohols or when reacting an olefin with an alcohol.

The invention will now be illustrated by the following examples.

EXAMPLES

Example 1

Synthesis of NUT-88 Zeolite with Hexane-1,6-bis (methylpyrrolidinium) bromide (HexPyrr)

The structure of hexane-1,6-bis (methylpyrrolidinium) bromide (HexPyrr) is as follows:

A reaction mixture with molar composition:

60 SiO$_2$: 2 Al$_2$O$_3$: 10 Na$_2$O: 10 HexPyrr: 3000 H$_2$O was prepared from:
- 48.07 g of "CAB-O-SIL" (BDH Ltd);
- 12.303 g of SoAl 235 solution (Laroche) (composition in weight %: 22.10% Al$_2$O$_3$; 20.40% Na$_2$O; 57.50% H$_2$O);
- 7.4 g of sodium hydroxide pellets;
- 57.2 g of HexPyrr (composition in weight %: 96.50% HexPyrr; 3.50% H$_2$O)
- 709 g of water.

The mixture was prepared using the following method:

A—solution of the sodium hydroxide and the sodium aluminate in water (approximately 200 g);
B—solution of the HexPyrr in water (approximately 150 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 13 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

$$100 \text{ SiO}_2: 4.82 \text{ Al}_2\text{O}_3: 0.337 \text{ Na}_2\text{O}.$$

The dried solid product was analysed by powder X ray diffraction and identified as NU-88 zeolite. The diagram obtained agreed with the results shown in Table 1. The diffractogram is shown in FIG. 1 [with the intensity I (arbitrary units) as the ordinate and 2θ (Cu K alpha) as the abscissa].

Example 2

Synthesis of NU-88 Zeolite with a Pentane-1,5-bis (methylpyrrolidinium) bromide (PentPyrr) Structure The structure of pentane-1,5-bis (methylpyrrolidinium) bromide (PentPyrr) is as follows:

A reaction mixture with molar composition:

$$60 \text{ SiO}_2: 1.714 \text{ Al}_2\text{O}_3: 12 \text{ Na}_2\text{O}: 10 \text{ PentPyrr}: 3000 \text{ H}_2\text{O}$$

was prepared from:
- 36.05 g of "CAB-O-SIL" (BDH Ltd);
- 7.908 g of SoAl 235 solution (Laroche) (composition in weight %: 22.10% Al$_2$O$_3$; 19.80% Na$_2$O; 58.10% H$_2$O);
- 7.6 g of sodium hydroxide pellets;
- 41.2 g of PentPyrr (composition in weight %: 97.02% PentPyrr; 2.98% H$_2$O)
- 532 g of distilled water.

The mixture was prepared using the following method:

A—solution of the sodium hydroxide and the sodium aluminate in water (approximately 150 g);
B—solution containing the PentPyrr in water (approximately 100 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 22 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

$$100 \text{ SiO}_2; 4.61 \text{ Al}_2\text{O}_3: 0.32 \text{ Na}_2\text{O}.$$

The dried solid product was analysed by powder X ray diffraction and identified as containing principally NU-88 zeolite, with traces of analcime (<5%); the diagram obtained agreed with the results shown in Table 1.

Example 3

Synthesis of NU-88 Zeolite with Pentpyrr

A reaction mixture with molar composition:

$$60 \text{ SiO}_2: 1.714 \text{ Al}_2\text{O}_3: 18 \text{ Na}_2\text{O}: 10 \text{ PentPyrr}: 3000 \text{ H}_2\text{O}$$

was prepared from:
- 48.07 g of "CAB-O-SIL" (BDH Ltd);
- 10.587 g of SoAl 235 solution (composition in weight %: 22.01% Al$_2$O$_3$; 19.81% Na$_2$O; 58.18% H$_2$O);
- 16.5 g of sodium hydroxide pellets;
- 55.3 g of PentPyrr (composition in weight %: 97.02% PentPyrr; 2.98% water)
- 708 g of distilled water.

The mixture was prepared using the following method:

A—solution of the sodium hydroxide and the sodium aluminate in water (approximately 200 g);
B—solution of the PentPyrr in water (approximately 150 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 15 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

$$100 \text{ SiO}_2: 5.10 \text{ Al}_2\text{O}_3: 0.153 \text{ Na}_2\text{O}.$$

The dried solid product was analysed by powder X ray diffraction and identified as NU-88 zeolite. The diagram obtained agreed with the results shown in Table 1.

Transmission electron microscopic analysis showed that the dominant morphology was characterized by crystals in the form of platelets which were bonded together to form aggregates. These platelets had the following approximate dimensions: 100×100×10 nm.

Example 4

Synthesis of NU-88 Zeolite with PentPyrr

The experiment described in Example 3 was repeated, the only difference being that a seed of NU-88 zeolite was added to the reaction mixture; the weight of the added seed was 4% by weight of the total quantity of silica used during the experiment.

A reaction mixture with molar composition:

60 SiO$_2$: 1.714 Al$_2$O$_3$: 18 Na$_2$O: 10 PentPyrr: 3000 H$_2$O was prepared from:
- 36.05 g of "CAB-O-SIL" (BDH Ltd);
- 7.805 g of SoAl 235 solution (composition in weight %: 22.39% Al$_2$O$_3$; 20.49% Na$_2$O; 57.12% H$_2$O);
- 12.3 g of sodium hydroxide pellets;
- 40.8 g of PentPyrr (composition in weight %: 97.99% organics; 2.01% H$_2$O)
- 532 g of water;
- 1.44 g of NU-88 (in the form of product prepared in Example 3).

The mixture was prepared using the following method:

A—solution of the sodium hydroxide and the sodium aluminate in water (approximately 150 g);
B—solution of the PentPyrr in water (approximately 100 g);
C—dispersion of the NU-88 seed in water (approximately 50 g);
D—dispersion of the CAB-O-SIL in the remaining water.

Solution A was added to dispersion D with stirring; solution B was then added, then dispersion C. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 9 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

100 SiO$_2$; 7.0 Al$_2$O$_3$: 1.26 Na$_2$O.

The dried solid product was analysed by powder X ray diffraction and identified as containing principally NU-88 zeolite, with a small amount of analcime (about 5%); the diagram obtained agreed with the results shown in Table 1.

Clearly, addition of the NU-88 seed to the reaction mixture reduced the total period for preparation of the NU-88 zeolite.

Example 5

Synthesis of NU-88 Zeolite with HexPyrr

A reaction mixture with molar composition:

60 SiO$_2$: 2 Al$_2$O$_3$: 18 Na$_2$O: 20 HexPyrr: 5000 H$_2$O was prepared from:
- 28.16 g of "CAB-O-SIL" (BDH Ltd);
- 13.388 g of sodium aluminate solution (composition in weight %: 11.90% Al$_2$O$_3$; 23.07% Na$_2$O; 65.02% H$_2$O);
- 7.3 g of sodium hydroxide pellets;
- 68.3 g of HexPyrr (composition in weight %: 94.75% organic; 5.25% H$_2$O);
- 689 g of distilled water.

The mixture was prepared using the following method:

A—solution of the sodium hydroxide and the sodium aluminate in water (approximately 200 g);
B—solution of the HexPyrr in water (approximately 150 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 11 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

100 SiO$_2$; 5.4 Al$_2$O$_3$: 2.64 Na$_2$O.

The dried solid product was analysed by powder X ray diffraction and identified as a mixture of NU-88 zeolite and analcime; the approximate composition was as follows: 85% NU-88/15% analcime.

Example 6

Synthesis of NU-88 Zeolite with PentPyrr

A reaction mixture with molar composition:

60 SiO$_2$: 1.50 Al$_2$O$_3$: 18 Na$_2$O: 10 PentPyrr: 3000 H$_2$O was prepared from:
- 45.06 g of "CAB-O-SIL" (BDH Ltd);
- 15.931 g of sodium aluminate solution (composition in weight %: 12.00% Al$_2$O$_3$; 24.44% Na$_2$O; 63.56% H$_2$O); 13.0 g of sodium hydroxide pellets;
- 50.4 g of PentPyrr (composition in weight %: 99.26% organic; 0.74% H$_2$O);
- 662 g of water.

The mixture was prepared using the following method:

A—solution of the sodium hydroxide and the sodium aluminate in water (approximately 200 g);
B—solution of the PentPyrr in water (approximately 150 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 12 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

100 SiO$_2$: 4.7 Al$_2$O$_3$: 0.20 Na$_2$O.

The dried solid product was analysed by powder X ray diffraction and identified as NU-88 zeolite; the diagram obtained agreed with the results shown in Table 1.

Example 7

Synthesis of NU-88 Zeolite with HexPyrr

A reaction mixture with molar composition:

60 SiO$_2$: 2 Al$_2$O$_3$: 18 Na$_2$O: 10 HexPyrr: 3000 H$_2$O was prepared from:
   36.05 g of "CAB-O-SIL";
   15.309 g of sodium aluminate solution (composition in weight %: 13.32% Al$_2$O$_3$; 24.43% Na$_2$O; 62.26% H$_2$O);
   9.6 g of sodium hydroxide pellets;
   43.2 g of HexPyrr (composition in weight %: 95.83% organic; 4.17% H$_2$O);
   616 g of distilled water.

The mixture was prepared using the following method:

A—solution of the sodium hydroxide and the sodium aluminate in water (approximately 200 g);
B—solution of the HexPyrr in water (approximately 150 g);
C—dispersion of the CAB-O-SIL in the remaining water.

Solution A was added to dispersion C with stirring. Solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred using an inclined paddle stirrer.

Samples of the reaction mixture were regularly removed and the progress of the reaction was followed by monitoring the pH. After 12 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

100 SiO$_2$: 6.54 Al$_2$O$_3$: 3.92 Na$_2$O.

The dried solid product was analysed by powder X ray diffraction and identified as a mixture of NU-88 zeolite and analcime; the approximate composition was as follows: 70% NU-88/30% analcime.

Example 8

Synthesis of NU-88 Zeolite with a Butane-1,4-bis (methylpyrrolidinium) bromide (TetraPyrr) Structure The structure of butane-1,4-bis (methylpyrrolidinium) bromide is as follows:

A reaction mixture with molar composition:

60 SiO$_2$: 1.5 Al$_2$O$_3$: 15 Na$_2$O: 10 TetraPyrr: 3000 H$_2$O was prepared from:
   24.03 g of "CAB-O-SIL" (BDH Ltd);
   9.711 g of sodium aluminate solution (composition in weight %: 10.52% Al$_2$O$_3$; 21.56% Na$_2$O; 67.92% H$_2$O);
   5.30 g of sodium hydroxide pellets;
   25.81 g of TetraPyrr (composition in weight %: 99.25% TetraPyrr; 0.25% H$_2$O);
   352.45 g of water.

The mixture was prepared using the following method:

A—solution of the sodium hydroxide and the sodium aluminate in water (approximately 120 g);
B—solution of the TetraPyrr in water (approximately 120 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. The mixture was stirred at 45 rpm using a rotor system.

After 10 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

100 SiO$_2$: 4.46 Al$_2$O$_3$: 2.72 Na$_2$O.

The dried solid product was analysed by powder X ray diffraction and identified as NU-88 zeolite.

Example 9

Synthesis of NU-88 Zeolite with a Butane-1,4-bis (bis-quinuclidinium) bromide (TetraBisQ) Structure The structure of butane-1,4-bis (bis-quinuclidinium) bromide is as follows:

A reaction mixture with molar composition:

60 SiO$_2$: 1.5 Al$_2$O$_3$: 10 Na$_2$O: 10 TetraBisQ: 3000 H$_2$O was prepared from:
   3.00 g of "CAB-O-SIL" (BDH Ltd);

1.214 g of sodium aluminate solution (composition in weight %: 10.52% $Al_2O_3$; 21.56% $Na_2O$; 67.92% $H_2O$);

0.33 g of sodium hydroxide pellets;

3.85 g of TetraBisQ (composition in weight %: 94.8% TetraBisQ; 5.2% $H_2O$);

43.94 g of distilled water.

The mixture was prepared using the following method:

A—solution of the sodium hydroxide and the sodium aluminate in water (approximately 11 g);
B—solution of the TetraPyrr in water (approximately 11 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 75 ml capacity. The mixture was heated to a temperature of 180° C. This temperature was maintained during the entire reaction period. The mixture was stirred at 45 rpm using a rotor system.

After 12 days at 180° C., the temperature of the reaction mixture was rapidly reduced to ambient temperature and the product was drained. The substance was then filtered; the solid product obtained was washed with demineralized water and dried for several hours at 110° C.

Analysis of the Si, Al and Na in the product was carried out using atomic emission spectroscopy. The following molar composition was determined:

100 $SiO_2$: 3.1 $Al_2O_3$: 0.65 $Na_2O$.

The dried solid product was analysed by powder X ray diffraction and identified as NU-88 zeolite.

Example 10

Synthesis of Ga-NU-88

A reaction mixture with molar composition:

60 $SiO_2$: 2 $Ga_2O_3$: 18 $Na_2O$: 10 HexPyrr: 3000 $H_2O$ was prepared from:

36.05 g of "CAB-O-SIL" (BDH Ltd);

21.872 g of sodium gallate solution (composition in weight %: 17.14% $Ga_2O_3$; 23.84% $Na_2O$; 59.01% $H_2O$);

7.7 g of sodium hydroxide pellets;

42.2 g of HexPyrr (composition in weight %: 99.01% organics; 1.99% $H_2O$);

524 g of distilled water.

The mixture was prepared using the following method:

A—solution of the sodium hydroxide and the sodium aluminate in water (approximately 150 g);
B—solution of the HexPyrr in water (approximately 100 g);
C—dispersion of the CAB-O-SIL in the remaining water.

Solution A was added to dispersion C with stirring; solution B was then added. Stirring was continued until a homogeneous gel was obtained. The mixture obtained was then transferred to a stainless steel autoclave with a 1 liter capacity. The mixture was heated to a temperature of 160° C. This temperature was maintained during the entire reaction period. Stirring was effected with an inclined paddle stirrer.

Samples of the reaction mixture were regularly removed and the progress of the reaction was followed by monitoring the pH. After 10 days at 160° C., the temperature of the reaction mixture was rapidly reduced to ambient temperature and the product was drained. The substance was then filtered; the solid product obtained was washed with demineralized water and dried for several hours at 110° C.

Analysis of the Si, Ga and Na in the product was carried out using atomic emission spectroscopy. The following molar composition was determined:

100 $SiO_2$: 5.35 $Ga_2O_3$: 1.07 $Na_2O$.

The dried solid product was analysed by powder X ray diffraction and identified as Ga-NU-88 zeolite; the diagram obtained agreed with the results shown in Table 1.

Example 11

Preparation of H-NU-88

A portion of the product from Example 3 was calcined in nitrogen for 24 hours at 550° C.; this step was immediately followed by a second calcining step in air, also at 550° C., for 24 hours.

The substance obtained was then brought into contact with an aqueous 1 molar solution of ammonium chloride for 2 hours at ambient temperature, using 50 ml of solution per gram of solid calcined product. The substance was then filtered, washed with deionized water and dried at 110° C. This treatment was repeated. The substance was then calcined in air for 24 hours at 550° C.

Analysis of the Si, Al and Na in the product, carried out using atomic emission spectroscopy, gave the following molar composition:

100 $SiO_2$: 4.05 $Al_2O_3$:<0.004 $Na_2O$.

Example 12

Preparation of H-NU-88

A portion of the product from Example 6 was calcined in nitrogen for 24 hours at 550° C.; this step was immediately followed by a second calcining step in air at 450° C. for 24 hours.

The substance obtained was then brought into contact with an aqueous 1 molar solution of ammonium chloride for 2 hours at ambient temperature, using 50 ml of solution per gram of solid calcined product. The substance was then filtered, washed with deionized water and dried at 110° C. This treatment was repeated. The substance was then calcined in air for 24 hours at 550° C. The calcined product was analysed by X ray diffraction. The diffractogram obtained is shown in FIG. 2 [$2\theta$ as the abscissa (Cu K alpha) and intensity I (arbitrary units) as the ordinate]. The X ray diffraction diagram was in agreement with Table 2.

Analysis of the Si, Al and Na in the product, carried out using atomic emission spectroscopy, gave the following molar composition:

100 $SiO_2$: 3.80 $Al_2O_3$: 0.011 $Na_2O$.

Example 13

Evaluation of the Catalytic Properties of H-NU-88 by Cracking Methylcyclohexane 1.2 g of H-NU-88 zeolite, prepared in Example 11, was introduced into a fixed bed tube reactor. The reactor temperature was raised to 500° C., then cyclohexane was introduced into the reactor. The diluting gas was nitrogen and the $N_2$/cyclohexane molar ratio admitted into the reactor was 12. The space velocity of methylcyclohexane, i.e., the mass of cyclohexane used per unit mass of H-NU-88 zeolite per unit of time, was such that it produced a 60% by weight conversion. The selectivities of the different products obtained are shown in the following table.

| Compounds | Selectivities (weight %) |
|---|---|
| Gas (C1 + C2 + C3 + C4) olefins and paraffins | 46.7 |
| C5–C6 compounds | 11.5 |
| C7 compounds, isomers of methylcyclohexane | 2.6 |
| Toluene + C8 + (1) | 39.2 |

(1) Compounds containing at least 8 carbon atoms.

This example shows that H-NU-88 zeolite is sufficiently active to crack methylcyclohexane and produce a gas (C1–C4) selectivity of 46.7% by weight for a conversion of 60% by weight.

What is claimed is:

1. A zeolite comprising:
    a chemical composition with the following formula, expressed in terms of the mole ratios of the oxides for the anhydrous state:

$$100\ XO_2,\ mY_2O_3,\ pR_{2/n}O$$

where
    m is 10 or less;
    p is 20 or less;
    R represents one or more cations with valency n;
    X represents silicon and/or germanium;
    Y is selected from the group consisting of aluminum, iron, gallium, boron, titanium, vanadium, zirconium, molybdenum, arsenic, antimony, chromium and manganese;
    said zeolite having an X ray diffraction diagram, in its as synthesized state, which comprises:

| $d_{hkl}$ ($10^{-10}$ m) | $I/I_{max}$ |
|---|---|
| 12.1 ± 0.35 | s or vs (1) |
| 11.0 ± 0.30 | s (1) |
| 9.88 ± 0.25 | m (1) |
| 6.17 ± 0.15 | w |
| 3.97 ± 0.09 | vs (2) |
| 3.90 ± 0.08 | vs (2) |
| 3.80 ± 0.08 | w (2) |
| 3.66 ± 0.07 | vw |
| 3.52 ± 0.07 | vw |
| 3.27 ± 0.07 | vw |
| 3.09 ± 0.06 | w |
| 2.91 ± 0.06 | w |
| 2.68 ± 0.06 | vw |
| 2.49 ± 0.05 | vw |
| 2.20 ± 0.05 | vw |
| 2.059 ± 0.05 | w |
| 1.729 ± 0.04 | vw | wherein the (1) peaks are not resolved and form a part of a feature, and the (2) peaks are not resolved and form part of a feature.

2. A zeolite according to claim 1, in which m is in the range 0.6 to 8.

3. A zeolite comprising:
    a chemical composition with the following formula, expressed in terms of the mole ratios of the oxides for the anhydrous state:

$$100\ XO_2\text{: 10 or less }Y_2O\text{: 10 or less }M_2O,$$

where
    X represents silicon and/or germanium;
    Y is aluminum, iron, gallium, boron, titanium, vanadium, zirconium, molybdenum, arsenic, antimony, chromium or manganese; and
    M is at least one alkali metal cation and/or ammonium and/or hydrogen;
    said zeolite having an X ray diffraction diagram, in its calcined state, which comprises:

| $d_{hkl}$ ($10^{-10}$ m) | $I/I_{max}$ |
|---|---|
| 12.1 ± 0.35 | vs (1) |
| 11.0 ± 0.30 | s or vs (1) |
| 9.92 ± 0.25 | w or m (1) |
| 8.83 ± 0.20 | vw |
| 6.17 ± 0.15 | w |
| 3.99 ± 0.10 | s or vs (2) |
| 3.91 ± 0.08 | vs (2) |
| 3.79 ± 0.08 | w or m (2) |
| 3.67 ± 0.07 | vw |
| 3.52 ± 0.07 | vw |
| 3.09 ± 06 | w |
| 2.90 ± 0.06 | w |
| 2.48 ± 0.05 | w |
| 2.065 ± 0.05 | w |
| 1.885 ± 0.04 | vw |
| 1.733 ± 0.04 | vw | wherein the (1) peaks are not resolved and form a part of a feature, and the (2) peaks are not resolved and form part of a feature.

4. A zeolite according to claim 1 with the following formula, expressed in terms of the mole ratios of the oxides for the anhydrous state:

$$100\ XO_2\text{: 10 or less }Y_2O_3\text{: 10 or less }Q\text{: 10 or less }M_2O,$$

where
X represents silicon and/or germanium;
Y is aluminum, iron, gallium, boron, titanium, vanadium, zirconium, molybdenum, arsenic, antimony, chromium or manganese;
M is at least one alkali metal cation and/or ammonium; and
Q is at least one organic nitrogen-containing cation or a precursor of an organic nitrogen-containing cation or a decomposition product of an organic nitrogen-containing cation.

5. A zeolite according to claim 4, in which:
Q is a bis (methylpyrrolidinium) cation or a decomposition product thereof or a precursor thereof, with the formula:

where n=4, 5 or 6, or Q is butane-1,4-bis (bisquinuclidinium) bromide, or a decomposition product thereof or a precursor thereof, with the following chemical formula:

6. A zeolite according to claim 4, in which Q is hexane-1,6 bis(methylpyrrolidinium) bromide, pentane-1,5-bis (methylpyrrolidinium) bromide, butane-1,4-bis (methylpyrrolidinium) bromide or butane-1,4 bis (quinuclidinium) bromide.

7. A zeolite according to claim 1, in which X is silicon and Y is aluminum.

8. A zeolite according to claim 1, at least partially in its H$^+$ form or in its NH$^+$ form or in its metal form, said metal being selected from the group consisting of groups IA, IB, IIA, IIB, IIIA, IIIB (including the rare earths), VIII, Sn, Pb and Si.

9. A process for the preparation of the zeolite of claim 1, comprising reacting and calcining an aqueous mixture comprising at least one source of at least one oxide $XO_2$, at least one source of at least one oxide $Y_2O_3$, and at least one nitrogen containing cation Q, or a precursor thereof, the mixture having the following molar composition:

$XO_2/Y_2O_3$ of at least 10;
$(R_{1/n})OH/XO_2$ of 0.01 to 2;
$H_2O/XO_2$ of 1 to 500;
$Q/XO_2$ of 0.005 to 1;
$L_pZ/XO_2$ of 0 to 5;
where
X is silicon and/or germanium;
Y is aluminum, iron, boron titanium, vanadium, zirconium, molybdenum, arsenic, antimony, gallium, chromium or manganese;
R is a cation with valence n which comprises Q;
$L_pZ$ is a salt, Z being an anion with valence p and L being an alkali metal ion or ammonium ion required to balance anion Z, and Z comprises an acid radical which is added in the form of a salt of L or an aluminum salt.

10. A process according to claim 9, in which:
Q is a bis (methylpyrrolidinium) cation or a precursor thereof, with the formula:

where n=4, 5 or 6, or Q is butane-1,4-bis (bisquinuclidinium) bromide, or a precursor thereof, with the following chemical formula:

11. A process according to claim 9, in which Q is hexane-1,6 bis(methylpyrrolidinium) bromide, pentane-1,5-bis(methylpyrrolidinium) bromide, butane-1,4-bis (methylpyrrolidinium) bromide or butane-1,4 bis (quinuclidinium) bromide.

12. A process according to claim 9, in which the aqueous medium comprises the salt $L_pZ$.

13. A process according to claim 9, further comprising calcining.

14. A process according to claim 9, further comprising H$^+$ or NH$^+$ exchange.

15. A process according to claim 9, further comprising exchanging a metal selected from the group consisting of IA, IIB, IIA, IIB, IIIA, IIIB (including the rare earths), VIII, Sn, Pb and Si.

16. A catalyst comprising the zeolite of claim 11 and a binder or at least one support or at least one other zeolite or at least one metal selected from the group consisting of the elements Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Re and Rh.

17. A hydrocarbon conversion process comprising subjecting a hydrocarbon feed to conditions sufficient to cause hydrocarbon conversion in the presence of a catalyst comprising the zeolite of claim 11.

18. A hydrocarbon conversion process according to claim 17, wherein the hydrocarbon feed comprises an alkylbenzene or a mixture of alkylbenzenes and the conditions sufficient to cause hydrocarbon conversion are isomerization conditions, in the vapor or liquid phase.

19. A hydrocarbon conversion process according to claim 17, wherein the hydrocarbon feed comprises xylene and the conditions sufficient to cause hydrocarbon conversion are isomerization or hydroisomerisation conditions.

20. A hydrocarbon conversion process according to claim 17, wherein the hydrocarbon feed comprises normal parafins containing 4 to 10 carbon atoms per molecule and the conditions sufficient to cause hydrocarbon conversion are hydroisomerisation conditions.

21. A hydrocarbon conversion process according to claim 17, wherein the hydrocarbon feed comprises olefin and the conditions sufficient to cause hydrocarbon conversion are isomerization conditions.

22. A hydrocarbon conversion process according to claim 17, wherein the conditions sufficient to cause hydrocarbon conversion are catalytic dewaxing conditions.

23. A hydrocarbon conversion process according to claim 17, wherein the hydrocarbon feed comprises one or more aromated alkylated compounds and the conditions sufficient to cause hydrocarbon conversion are dismutation and/or transalkylation conditions in the vapor or liquid phase.

24. A hydrocarbon conversion process according to claim 23, wherein the hydrocarbon feed comprises xylene.

25. A hydrocarbon conversion process according to claim 23, wherein the hydrocarbon feed comprises toluene and aromatic compounds.

26. A hydrocarbon conversion process according to claim 17, wherein the hydrocarbon feed comprises an olefinic or aromatic compound and the conditions sufficient to cause hydrocarbon conversion comprise contacting the olefinic or aromatic compound with a suitable alkylating compound under alkylating conditions, in the vapor or in the liquid phase.

27. A hydrocarbon conversion process according to claim 17, wherein the hydrocarbon feed comprises unsaturated compounds or on saturated compounds or on mixtures of hydrocarbons and the conditions sufficient to cause hydrocarbon conversion are oligomerisation, cyclisation and/or aromatisation conditions.

28. A hydrocarbon conversion process according to claim 17, wherein the conditions sufficient to cause hydrocarbon conversion are cracking conditions.

29. A hydrocarbon conversion process according to claim 17, wherein the conditions sufficient to cause hydrocarbon conversion are hydrogenation and/or dehydrogenation conditions.

30. A catalyst comprising the zeolite of claim 3 and a binder or at least one support or at least one other zeolite or at least one metal selected from the group consisting of the elements Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Re and Rh.

31. A catalyst comprising the zeolite of claim 4 and a binder or at least one support or at least one other zeolite or at least one metal selected from the group consisting of the elements Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Re and Rh.

32. A hydrocarbon conversion process comprising subjecting a hydrocarbon feed to conditions sufficient to cause hydrocarbon conversion in the presence of a catalyst comprising the zeolite of claim 3.

33. A hydrocarbon conversion process comprising subjecting a hydrocarbon feed to conditions sufficient to cause hydrocarbon conversion in the presence of a catalyst comprising the zeolite of claim 4.

34. A process for the preparation of the zeolite of claim 3, comprising reacting and calcining an aqueous mixture comprising at least one source of at least one oxide $XO_2$, at least one source of at least one oxide $Y_2O_3$, optionally at least one source of at least one oxide $M_2O$, and at least one organic nitrogen-containing cation Q or a precursor thereof, the mixture having the following molar composition:

$XO_2/Y_2O_3$ of at least 10;

$Q/XO_2$ of 0.005 to 1;

$H_2O/XO_2$ of 1 to 500;

$L_pZ/XO_2$ of 0 to 5;

where

X is silicon and/or germanium;

Y is aluminum, iron, boron titanium, vanadium, zirconium, molybdenum, arsenic, antimony, gallium, chromium or manganese;

$L_pZ$ is a salt, Z being an anion with valence p and L being an alkali metal ion or ammonium ion which is the same as M or a mixture of M and a further alkali metal ion or ammonium ion required to balance anion Z, and Z comprises an acid radical which is added in the form of a salt of L or an aluminum salt.

35. A process for the preparation of the zeolite of claim 4, in which an aqueous mixture is reacted, said aqueous mixture comprising at least one source of at least one oxide $XO_2$, at least one source of at least one oxide $Y_2O_3$, optionally at least one source of at least one oxide $M_2O$, and at least one organic nitrogen-containing cation Q, or a precursor thereof, the mixture having the following molar composition:

$XO_2/Y_2O_3$ of at least 10;

$H_2O/XO_2$ of 1 to 500;

$Q/XO_2$ of 0.005 to 1;

$L_pZ/XO_2$ of 0 to 5;

where

X is silicon and/or germanium;

Y is aluminum, iron, boron titanium, vanadium, zirconium, molybdenum, arsenic, antimony, gallium, chromium or manganese;

$L_pZ$ is a salt, Z being an anion with valence p and L being an alkali metal ion or ammonium ion which is the same as M or a mixture of M and a further alkali metal ion or ammonium ion required to balance anion Z, and Z comprises an acid radical which is added in the form of a salt of L or an aluminum salt.

\* \* \* \* \*